United States Patent [19]

Graziano

[11] 4,275,748

[45] Jun. 30, 1981

[54] METHOD AND COMPOSITION FOR MODIFYING FILAMENTOUS KERATINS

[76] Inventor: Helen V. Graziano, 332 W. Kathleen Dr., Park Ridge, Ill. 60068

[21] Appl. No.: 116,054

[22] Filed: Jan. 28, 1980

[51] Int. Cl.$^3$ ............................................. A45D 7/00
[52] U.S. Cl. ...................................................... 132/7
[58] Field of Search ................ 132/7; 424/71, 72, 70, 424/DIG. 2, 359, 360, 329; 8/94.1 R, 111; 252/545, 105; 106/193 D

[56] References Cited

U.S. PATENT DOCUMENTS

| | | | |
|---|---|---|---|
| 2,390,073 | 12/1945 | Calva | 132/7 |
| 2,540,494 | 2/1951 | Schwarz | 132/7 |
| 2,691,378 | 10/1954 | Oliva | 132/7 |
| 3,683,939 | 8/1972 | Johnsen | 132/7 |
| 3,911,106 | 10/1975 | Scott | 132/7 |

*Primary Examiner*—G. E. McNeill
*Attorney, Agent, or Firm*—Neuman, Williams, Anderson & Olson

[57] ABSTRACT

A composition and method for modifying filamentous keratins. Filamentous keratins are contacted with an effective amount of a modifying composition consisting essentially of:

from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80.

The composition is allowed to remain in contact with the filamentous keratins for a period of time sufficient to effect modification thereof. The composition is then removed from the filamentous keratins, and the keratins are cleansed by contact with water-soluble cleansing composition, which cleansing composition is removed after cleansing is effected. The composition and method and particularly efficacious in the straightening of filamentous human keratins.

10 Claims, No Drawings

METHOD AND COMPOSITION FOR MODIFYING FILAMENTOUS KERATINS

BACKGROUND OF THE INVENTION

1. Field of the Invention

This invention relates generally to the modification of filamentous keratins, and relates more particularly to the modification and straightening of filamentous human keratins and compositions having ideal properties for such purpose.

2. Description of the Prior Art

The use of compositions to modify filamentous keratins such as human hair and wool has long been known. The known modifications of such filamentous keratins include, for example, the straightening of said keratins which are naturally wavy, frizzy, curly or kinky, and the conversion of naturally straight keratins to a wavy or curly state.

A typical example of the modification of filamentous human keratins or hair is the permanent waving of hair. It is well known that human hair can be set into a permanent wave by establishing a directed stress or deformation on the hair in the form of the desired wave, curl or other configuration, applying a reducing agent such as a solution of ammonium thioglycolate for a short time, rinsing out the reducing agent, and then treating the hair with a oxidizing agent such as sodium bromate solution or hydrogen peroxide. Many of the known procedures and compositions require the simultaneous use of heat with the waving composition, e.g., Oliva, U.S. Pat. No. 2,691,378, to cause or otherwise speed the permanent waving action of the composition.

During the initial treatment with the reducing agent, the natural stress in the hair is temporarily alleviated or minimized by the opening up of the cystine disulfide linkages found in the filamentous keratins. Upon oxidation, cystine bonds are again formed by closing of disulfide linkages, but now the closure occurs not with the original sulfhydryl groups liberated, but with those which have been brought into greater proximity as a result of the directed stress. The filamentous keratins reform, but they now retain the new waved structure as a permanent feature of the hair until either a new waving procedure is performed, or until the hair grows out.

The disadvantages of such permanent waving techniques are also well known, and include damage to the filamentous keratins and cuticles of those keratin filaments in the nature of loss of strength and brittleness, which in turn leads to difficulty in combing and breakage near the scalp; dryness and lack of lustre and sheen in the hair; inability to treat waved hair with other lotions and conditioners after waving; adverse affects resulting from the necessity of heating the filamentous keratins to produce waving; and the complexity of the procedures and compositions used, which comprise multiple solutions (reducing agent, oxidizing agent) which must be prepared and used in sequence, and which are often strong chemicals which must be carefully handled to avoid damage to the hair, scalp and hands of the individual(s) involved in the process.

Hair damage from permanent waving can, however, be somewhat ameloriated by the use of known conditioners, such as shown in Johnsen et al., U.S. Pat. No. 3,683,939, applied concurrently with the waving solutions or as a separate treatment.

Another example of the modification of filamentous human keratins or hair is the permanent straightening of wavy, frizzy, curly or kinky hair. The straightening of hair, however, in comparison with imparting a permanent wave or curl, is usually a more rigorous, severe process, particularly when permanent straightening of curly or kinky hair is required. The compositions known to the art for straightening usually comprise concentrated and dangerous reducing substances, particularly caustic soda or sodium hydroxide, to open up the cystine disulfide linkages in the filamentous keratins, which substances, if not used with extreme care, can severely damage and break the hair being treated, as well as burn the scalp of the individual whose hair is being treated. See, e.g., Calva, U.S. Pat. No. 2,390,073. As in permanent waving, permanent straightening compositions usually comprise multiple solutions, including a reducing agent solution and an oxidizing agent solution, and many of the known compositions require concurrent use of heat.

The disadvantages of the known permanent straightening solutions mirror those of permanent waving compositions, but are more magnified. Permanently straightened filamentous human keratins or hair is often severely damaged by the straightening process, suffering cuticle damage, loss of strength, and major breakage, both along the hair shaft and at the scalp line. Lustre, sheen, body and texture of the hair are very poor after use of conventional straighteners. It is also very difficult to straighten hair with the known compositions which has previously been dyed, tinted, bleached, double process bleached or otherwise treated, and any attempt to straighten hair immediately after bleaching or tinting with those compositions will result in severe breakage and damage. The complexity of procedures and multiple liquid compositions that must be used is also extremely disadvantageous, particularly as the strength of the reducing solutions is such as to hold out the potential for hand and scalp burns and injury. The strength of solutions used also requires careful control of contact time with the hair to prevent injury. With an individual with fragile hair or sensitive scalp, the known permanent straightening compositions often have to be removed before the desired degree of straightening of the hair occurs to prevent damage and burns.

A further disadvantage with known filamentous human keratin permanent straightening compositions is that the strength of reducing and oxidizing agents used renders unsatisfactory attempts to ameloriate hair damage by incorporating known conditioners into the straightening process, either concurrently with application of the reducing agent, or following application and removal of the oxidizing agent.

The optimum combination of properties for an ideal filamentous human keratins or hair modifying composition, particularly one useful for straightening wavy, frizzy, curly or kinky filamentous human keratins or hair, is such that:

(1) the composition must be sufficiently strong to effect any desired degree of modification or straightening without damage to the filamentous human keratins or hair, yet be in such form that it may be applied without injury to the skin or scalp of the individual whose hair is being straightened;

(2) the composition must be usable on filamentous human keratins or hair previously dyed, tinted, bleached, double process bleached or otherwise treated, and be capable of causing the desired modification or straightening to such keratins essentially without damage or breakage;

(3) the composition must obviate or minimize damage and breakage to the filamentous human keratins or hair, and must preserve and if possible enhance the strength, lustre, sheen, body and texture thereof;

(4) the composition must be safe and easy to compound and apply to the filamentous human keratins or hair, preferably consisting of a single solution or composition which may be applied in one contacting with the filamentous human keratins or hair, must be effective without any necessary application of heat, and should require no after-treatment with a chemical neutralizer or conditioning composition; and (5) the composition must provide permanent modification, particularly straightening, of the filamentous human keratins or hair, said modification continuing without the necessity for additional treatment until a new modification procedure is performed, or until the hair grow out.

None of the modifying compositions for filamentous keratins known to the art, however, particularly none of those known to be useful for the straightening of filamentous human keratins or hair, provide this optimum combination of properties desirable with respect to modification of filamentous human keratins or hair.

SUMMARY OF THE INVENTION

The present invention relates to a method and compositions for modifying filamentous keratins. The method consists of the application of an effective amount of a modifying composition to the filamentous keratins, thereafter allowing the composition to remain in contact with the filamentous keratins for a period of time sufficient to effect modification, removing the composition from said filamentous keratins, cleansing said filamentous keratins by contacting said keratins with a water-soluble cleansing composition, and removing said cleansing composition after cleansing is effected.

The modifying compositions of the present invention consists essentially of the following components:
from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80.

The present invention overcomes the drawbacks of the prior art by providing a method of and compositions for modifying filamentous keratins, particularly human hair, which utilizes one safe and easy to apply composition, requires no heating or after-treatment with a chemical neutralizer or conditioner, is of such form and consistency such that it may be applied so as to readily avoid injury to the skin or scalp, is capable of permanently effecting modification, including straightening, to any desired degree, is effective in modifying previously dyed, tinted, bleached, double process bleached or otherwise treated filamentous keratins without causing damage or breakage, and which essentially obviates damage and breakage to the filamentous keratin, while preserving the strength, lustre, sheen, body and texture thereof.

Accordingly, it is an object of this invention to provide an improved method of permanently modifying filamentous keratins, particularly human hair, comprising a method of straightening wavy, frizzy, curly or kinky filamentous keratins to any desired degree, which is safe, simple, and requires no application of heat or after-treatment with a chemical neutralizer or conditioner.

It is a further object of this invention to provide a composition which permanently modifies filamentous keratins, particularly human hair, which is especially efficacious in effecting straightening of wavy, frizzy, curly or kinky filamentous keratins to any desired degree, and which is capable of effecting said modification without damage to the filamentous keratin, yet is of such form and consistency that it may be applied without injury to the skin or scalp of the individual whose hair is being straightened.

It is another object of this invention to provide a modifying composition which essentially obviates damage and breakage to filamentous keratins, particularly human hair, during and as a result of modification or straightening, and which preserves and enhances the lustre, sheen, body and texture of said keratins.

It is a further object of this invention to provide a modifying composition which modifies and is especially efficacious for straightening filamentous keratins, particularly human hair, which has previously been dyed, tinted, bleached, double process bleached or otherwise treated, essentially without damage or breakage to said keratins.

Other objects and advantages of this invention will become apparent upon reading the following detailed description and appended claims.

DESCRIPTION OF THE PREFERRED EMBODIMENT

The preferred method of the invention provides for the modification of filamentous keratins, particularly human hair, and is especially efficacious in the straightening, to any desired degree, of wavy, frizzy, curly or kinky filamentous keratins. The method comprises contacting the filamentous keratins with an effective amount of a modifying composition consisting essentially of:
from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80;
thereafter allowing said composition to remain in contact with said filamentous keratins for a period of time sufficient to effect modification thereof, removing said composition from said filamentous keratins by rinsing in cold water, cleansing said filamentous keratins by contacting them with a water-soluble cleansing composition, such as a commercially available acid-balanced shampoo having a pH of from about 4.5 to 5.5, and removing said cleansing composition after cleansing is effected by a further rinsing with water.

An "effective amount" of the modifying composition of the invention is an amount sufficient to coat the complete surface of each filamentous keratin or hair throughout its total longitudinal and circumferential extent.

The preferred method for straightening filamentous human keratins or hair comprises contacting said keratins with an effective amount of the modifying composition by applying the composition with a plastic spatula on small partings of the hair close to the scalp, then down from one and one-half to three inches along the hair shafts, comprising a distance sufficient to cover any new growth of filamentous keratins, applying a longitudinal stress to said filamentous keratins, such as by combing, while distributing the composition completely through each parted section of filamentous keratins with a smooth tooth, hard rubber tail comb, while maintaining the modifying composition in contact therewith, thereafter allowing said composition to remain in contact with said filamentous keratins for a period of time sufficient to effect straightening thereof, usually from about 5 to about 25 minutes, removing said composition from said filamentous keratins by rinsing with cold water, cleansing said filamentous keratins by contacting said keratins with a water-soluble cleansing composition or shampoo, most preferably a commercially available acid-balanced shampoo having a pH of from about 4.5 to 5.5, and removing said cleansing composition after cleansing is effected by a further rinsing with water. If the cleansing composition is applied in multiple latherings, it is preferred that the final lathering be carried out with said acid-balanced shampoo. A cream rinse may thereafter be used, if necessary, unless the shampoo contains components to provide a detangling function. It may also be advantageous, where long filamentous human keratins are being straightened, to simultaneously apply an additional conditioner on at least the old growth of the filaments, to avoid tangling and to maintain hair moisture during straightening.

Use of the acid-balanced cleansing shampoo, as either the sole cleansing composition or for a final lathering, serves to remove any deleterious alkaline residues remaining from contact with the modifying composition, decreases the stripping effects of the shampoo, and the resulting lower keratins pH simultaneously improves gloss, softness, combing ease and manageability.

Variations of the preferred method apparent to those skilled in the cosmetic and beautician arts may also be practiced. The modifying composition may be reapplied and distributed in a second application of an effective amount thereof, and the keratins again subjected to longitudinal stress, for improved conditioning and more complete modification of the hair. The composition of the invention may also be initially applied throughout the longitudinal extent of the hair filaments, rather than just in the immediate area of new growth. The application of longitudinal stress through combing may utilize any known combing technique which works the hair filaments, yet avoids deposition of the composition on the scalp.

The preferred composition for modifying filamentous keratins, particularly human hair, consists essentially of:
from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80.

The particularly preferred methods and compositions for modifying filamentous keratins, including human hair, and in particular straightening said keratins or hair, are those methods hereinbefore described in which the following approximate compositions are utilized:

TABLE 1

| Constituent | Composition* | | |
|---|---|---|---|
| | I | II | III |
| water | 58.47 | 58.65 | 58.83 |
| milk protein product | 19.49 | 19.55 | 19.61 |
| polysaccharide | 6.09 | 6.11 | 6.13 |
| sodium hydroxide | 6.09 | 5.80 | 5.52 |
| polyglycerol | 4.875 | 4.89 | 4.90 |
| aqueous collagen polypeptide/amino acid solution | 4.875 | 4.89 | 4.90 |
| polysorbate-80 | .09 | .09 | .09 |

*weight percent.

By use of compositions I, II and III, variation in degree of straightening may be afforded. Composition I provides maximum strength for the most severe straightening of wavy, frizzy, curly or kinky filamentous keratins. Composition II is a slightly weaker modifying composition, and is particularly useful where it is desirable to avoid a total straightening or complete removal of curl from filamentous keratins, yet effect substantial straightening. Composition III is further reduced in strength from Composition II, and is most advantageously used where only a slight straightening of the filamentous keratins is desired. Composition III is also particularly useful for straightening of filamentous keratins which have previously been dyed, tinted, bleached, double process bleached or otherwise treated, allowing such keratins to be straightened with essentially no breakage or damage. Use of Composition III thus allows the coloration, tinting or bleaching of filamentous keratins to be carried out before straightening, even immediately prior to application of the composition of the invention, without weakening of the filaments, and with straightening resulting all the way to the base of said colored, tinted or bleached filaments.

Filamentous keratins which have previously dyed, tinted, bleached, double process bleached or otherwise treated, and which exhibit severe damage or extremely poor condition, may be treated with composition III in which an additional conditioning oil known to those skilled in the cosmetic and beautician arts, such as Livol, manufactured by Jheri Redding Products, has been combined prior to application to the filamentous keratins.

Further, severely damaged bleached filamentous human keratins may also require some variation in the method of the invention, in that the partings may be taken in circumferential bands or layers about the head, and the modifying composition sequentially applied and the straightening of such bands or layers individually completed to minimize the possibility of further damage and maximize the restoration of hair quality. This layered technique may also be used, if desired, whenever the method of the invention is practiced.

Compositions I to III may also be utilized on filamentous keratins previously straightened or permanently waved by other techniques without damaging the filaments. A further straightening may thus be carried out, or the wave or curl imparted by the permanent waving technique may be removed or straightened to the desired degree.

Combined use of two or all of compositions I to III may also be practiced, such as composition I being initially utilized for the major longitudinal extent of the filamentous keratins, and composition III being used for modification of the ends of the filaments.

Use of the preferred modifying compositions and methods of the invention results in a permanent modification of the filamentous keratins, particularly human hair. The modified keratins retain their form, e.g., straightened over their natural configuration, until a further treatment is performed or, in the case of filamentous human keratins, until new growth from the scalp occurs; that much of the hair previously straightened maintains its modified form, but straightening of the new growth must be effected, the interval between application of the composition of the invention to such new growth being dependent on the rate of growth, the length of the hair, and the particular texture of the hair, including the degree of natural kink or curl. In most cases, an interval of about three months to a year's duration is afforded before new growth straightening must be effected.

The method and compositions of the invention are effective on every type and texture of filamentous human keratins or hair, including hair previously damaged by other treatments. Growth and quality of human hair damaged by breakage due to prior treatments with other straightening or permanent wave compositions is surprisingly found to be aided by contact with the modifying compositions of the invention; hair that was dull, dry, and brittle prior to treatment becomes lustrous and smooth, as well as straightened. In severe cases of previous damage and breakage, however, a known conditioning agent or composition may be applied to the filamentous keratins prior to modification by the method and compositions of the invention.

In even the most rigorous and severe modifications of filamentous keratins, including total straightening of tightly curled or kinky human hair, modification by the method and compositions of the invention is carried out with none or essentially no damage or breakage to the keratins. The strength, lustre, sheen, and texture of the keratins is maintained and enhanced, such that the straightened hair is soft, shiny and smooth, yet permanently modified or straightened. The composition clearly conditions the hair as it straightens, leaving the hair in better condition than before straightening.

Damage to the individual's skin and scalp where filamentous human keratins are modified is avoided due to the highly viscous, butter-like consistency of the modifying compositions of the invention. The composition demonstrates a previously unknown property with respect to modifying compositions, particularly straightening compositions, of remaining where it is placed on the keratins, either by direct application or as transferred through combing, with virtually no migration by gravity, flow, melting as a result of body or ambient heat or otherwise. The compositions do not splatter, drip or run down the filaments to the scalp, and thus the log-standing problems of burning and skin damage formerly experienced with straightening are not presented.

The individual components of the compositions of the invention are all readily available materials. The water utilized may be ordinary tap water, and no additional deionization or other treatment is usually required. If particularly hard or mineral-laden water must be utilized, however, treatment by use of an activated charcoal or equivalent filter, or by use of commercially available water-softening apparatus, may be advantageous in order to minimize the formation or presence of salts and other compounds which may reduce the efficacy of the compositions, and possibly deposit on the filamentous keratins, resulting in dullness and hardness.

The milk protein product component utilized may be either liquid milk or milk products, such as homogenized milk, or reconsituted or redissolved powdered milk or milk products.

The polysaccharide utilized may be any readily available starch, dextrin or glycogen. Corn starch is particularly useful as the polysaccharide component of the compositions of the invention.

The sodium hydroxide utilized may be any readily available material having a purity acceptable for pharmaceutical, technical or general chemical application. Any sodium hydroxide satisfying USP or FDA purity restrictions is suitable for use in these compositions.

The polygycerol utilized may include commercially available glycerols and polyglycerols, as well as such materials as ordinary food grade cooking or kitchen lard, which is particularly useful in preparing these compositions.

The aqueous solution of collagen polypeptides and amino acids useful in the preparation of the compositions of the invention comprises a conditioning agent of the type well known to those skilled in the cosmetic and beautician arts. A particular preferred solution is PPT S-77®, manufactured by Redken Laboratories, Canoga Park, Calif., sold as an acid-balanced hair reconditioner, which comprises an aqueous solution of collagen polypeptides and amino acids.

The polysorbate-80 is a known, water-soluble material used often in cosmetic preparations.

As a further useful but non-essential component, food color may be added to the compositions of the invention. Any acceptable food grade colorant materials, singly or in combination, which provide a pleasing color to the composition may be used. A mixture of FDC #40 and FDC #3 is particularly useful to impart a neutral, tan color to the compositions. Other additional conditioners, oil treatments, and adjuvants known to the cosmetic and beautician arts may also be incorporated where desirable, though such incorporation is unnecessary to effective practice of the invention.

The mechanism by which the compositions of the invention effect modification of filamentous human keratins or hair, particularly straightening, with none or essentially no breakage or damage to the hair, is not completely understood. No separate oxidizing agent need be used, however, and chemical neutralization after modification is not necessary.

Without wishing to be bound by this explanation, it appears that the unique combination and proportions of components of the compositions of the invention results in cystine disulfide break down and later reformation in the filamentous keratins, resulting in severe straightening of even tightly curled and kinked filamentous human keratins, while surprisingly preserving and even improving the strength, lustre, sheen and texture of the keratins, without burning, damage or breakage. The sodium hydroxide reducing agent softens the keratin cuticle, partially stretching the hair filament and permitting the composition to permeate to the cortex of the hair, where it breaks the cystine disulfide bonds and disrupts and relaxes the internal helical structure of the hair, particularly when longitudinal stress is applied to the hair.

Atmospheric oxygen is the apparent oxidizing agent, reoxidation taking place during contact with and on removal of the composition. The milk protein product acts, together with at least the aqueous collagen polypeptide/amino acid solution, to simultaneously protect and recondition the filamentous keratins, with the polyglycerol and polysaccharide serving to prevent conditioner degradation and ineffectualness caused by the sodium hydroxide presence, and possibly as further aids to both the keratin modification and conditioning.

The result is modification of filamentous human keratins, particularly straightening, to any desired degree, with no damage to the keratins, and with concomitant preservation and enhancement of the keratins' appearance.

The following examples illustrate the method and compositions of the invention:

EXAMPLE 1

Preparation of First Modifying Composition of the Invention, and Straightening of Filamentous Human Keratins A. The following quantities of component materials were measured into containers:
58.47 weight percent water;
19.49 weight percent milk protein product (homogenized milk);
6.09 weight percent polysaccharide (corn starch);
6.09 weight percent sodium hydroxide;
4.875 weight percent polyglycerol (lard);
4.875 weight percent aqueous collagen polypeptide/amino acid solution (PPT S-77 ®, Redken Laboratories)
0.09 weight percent polysorbate-80; and
0.02 weight percent food coloring (mixture of FDC #40+FDC #3).

One third of the water was thereafter added to the entire quantity of sodium hydroxide in an enamel pot, and the mixture was stirred until smooth. The remaining two thirds of the water was added to the polysaccharide in an enamel pot, and this mixture was stirred until smooth. The total quantity of polyglycerol was placed in a third enameled pot and placed on a gas burner with heat diffuser at high heat until melted, a period of approximately 7 minutes; the pot was then removed from the heat and allowed to cool for 7 minutes.

On completion of the cooling period, the water/sodium hydroxide mixture was added slowly, with constant stirring, to the polyglycerol; half of the water/polysaccharide mixture was then added to the polyglycerol/water/sodium hydroxide mixture. This combined mixture was then replaced on the gas burner, the remaining water/polysaccharide mixture was slowly added thereto with stirring, and the total combination was stirred until thoroughly mixed.

The food coloring, aqueous collagen polypeptide/amino acid solution, and milk protein product were then added sequentially to the preceding mixture with thorough stirring, and the new total combination was stirred until smooth and slightly viscous. The mixture was then heated for an additional 15 minute period, removed from the burner, and the polysorbate-80 was added slowly thereto and the composition mixed thoroughly. The completed composition was then poured into storage containers and left uncovered for 24 hours to set before said containers were sealed. The final composition had a thick, viscous, butter-like consistency.

B. The composition prepared in part A. was thereafter used to straighten naturally tightly curled and kinked filamentous human keratins.

The easy to handle, butter-like composition was applied with a plastic spatula on small partings of the subject individual's hair close to the scalp, then down the hair shaft for a distance of one and one-half to three inches, depending on the hair length and extent of new growth. The composition was then combed through each parted section of hair with a smooth tooth, hard rubber tail comb, so as to completely cover the hairs and work the composition through the entire length of the strands. The application and combing action permits the cuticle to soften and the composition to enter the hair cortex. The longitudinal stress placed on the hair by the combing resulted in the stretching and straightening of the hair, individual hairs stretching up to one-fifth their length without damage. The composition was allowed to remain on the hair after combing without any application of heat whatsoever for approximately 25 minutes without causing any scalp burning or injury of any sort, the conditioning properties of the composition further preventing hair damage despite such severe straightening. The desired degree of straightening was controlled in part by regulating the contact time of the composition with the hair.

The hair was then rinsed thoroughly with cold water. A cleansing composition was then applied, utilizing an acid-balanced shampoo having a pH of from about 4.5 to 5.5, and thereafter removed by rinsing with water. No application of chemical neutralizer of any sort was applied, nor was any necessary. Due to the length of the subject hair, a cream rinse was thereafter applied to detangle the hair.

After straightening, the hair showed no residual kink or curl, a condition which was maintained for over three months. The hair was soft and manageable, and demonstrated excellent strength, lustre and shine, with essentially no breakage whatsoever.

Repetition of straightening at approximately three-month intervals of the same subject individual's hair resulted in maintenance of the desired hair straightness and quality with essentially no breakage whatsoever. The hair continued to be soft and manageable, with excellent strength, lustre and shine.

Repetition of this procedure on another subject individual having similarly kinked and curled hair, which however had been previously straightened by another process and was dull, somewhat coarse and dry, produced virtually identical results, with a noticeable enhancement of hair quality and appearance and essentially no breakage, despite the hair's initially damaged condition.

EXAMPLE 2

Preparation of Second Modifying Composition of the Invention, and Straightening of Filamentous Human Keratins A. A modifying composition containing the following component materials was prepared by the procedure of Example 1, part A:
58.65 weight percent water;
19.55 weight percent milk protein product (homogenized milk);
6.11 weight percent polysaccharide (corn starch);
5.80 weight percent sodium hydroxide;
4.89 weight percent polyglycerol (lard);

4.89 weight percent aqueous collagen polypeptide/amino acid solution (PPT S-77 ®, Redken Laboratories);
0.09 weight percent polysorbate-80; and
0.02 weight percent food coloring (mixture of FDC #40+FDC #3).

B. Following the procedure set out in Example 1, part B, the composition prepared here in part A. was thereafter used to straignten naturally curled and wavy filamentous human keratins. In contrast to Example 1, the subject individual wished to allow some degree of the natural curl and wave to remain in the hair, while enjoying substantial straightening. The composition was allowed to remain on the hair after combing for approximately 20 to 25 minutes, with the hair then being rinsed and a cleansing shampoo applied, as set out in Example 1, part B.

The hair showed a marked preservation of the natural wave after straightening, yet was predominantly devoid of curl. The hair was again soft and manageable, and demonstrated excellent strength, lustre and shine, with essentially no breakage whatsoever. The straightened condition of the hair before repetition of the straightening procedure of the invention was maintained for a period in excess of four months.

EXAMPLE 3

Preparation of Third Modifying Composition of the Invention, and Straightening of Filamentous Human Keratins A. A modifying composition containing the following component materials was prepared by the procedure of Example 1, part A:
58.83 weight percent water;
19.61 weight percent milk protein product (homogenized milk);
6.13 weight percent polysaccharide (corn starch);
5.52 weight percent sodium hydroxide;
4.90 weight percent polyglycerol (lard);
4.90 weight percent aqueous collagen polypeptide/amino acid solution (PPT S-77 ®, Redken Laboratories);
0.09 weight percent polysorbate-80; and
0.02 weight percent food coloring (mixture of FDC #40+FDC #3).

B. Following the procedure set out in Example 1, part B, the composition prepared here in part A. was thereafter used to partially straighten naturally mildly curled filamentous human keratins. In contrast to Example 1, the subject individual had mildly curled hair, and wished to only slightly straighten the natural curl, without substantial straightening. The composition was allowed to remain on the hair after combing for between 20 and 25 minutes, with the hair then being rinsed and a cleansing shampoo applied, as set out in Example 1, part B.

The hair showed only a minimal yet noticeable relaxation of the natural curl after straightening, and the hair was again left soft and manageable, with excellent strength, lustre and shine, and with no noticeable breakage whatsoever. The straightened condition of the hair before repetition of the straightening procedure of the invention was maintained for a period in excess of four months.

C. Following the procedure set out in Example 1, part B, the composition prepared here in part A. was further used to straighten naturally curled and waved filamentous human keratins which had previously been bleached and toned. The subject individual had moderately curled and waved hair, and desired a substantial straightening. The composition was allowed to remain on the hair after combing for approximately 5 to 10 minutes, with the hair then being rinsed and a cleansing shampoo applied, as set out in Example 1, part B.

The hair showed a substantial straightening of the bleached and toned hair, yet there was essentially no hair breakage, straightening extended to the scalp, and the hair was once again soft and manageable, while demonstrating superior strength, lustre and shine. The straightened condition of the hair before repetition of the straightening procedure of the invention was maintained for a period in excess of four months.

While particular embodiments of the invention, and the best mode contemplated by the inventor for carrying out the invention, have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

I claim:

1. A method of modifying filamentous keratins which comprises contacting said keratins with an effective amount of a modifying composition consisting essentially of:
from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80;
thereafter allowing said composition to remain in contact with said filamentous keratins for a period of time sufficient to effect modification thereof, removing said composition from said filamentous keratins, cleansing said filamentous keratins by contacting said keratins with a water-soluble cleansing composition, and removing said cleansing composition after cleansing is effected.

2. A method of straightening filamentous human keratins which comprises contacting said keratins with an effective amount of a modifying composition consisting essentially of:
from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80;
applying longitudinal stress to said filamentous keratins while maintaining said modifying composition in contact therewith, thereafter allowing said composition to remain in contact with said filamentous keratins for a period of time sufficient to effect straightening thereof, removing said composition from said filamentous keratins, cleansing said filamentous keratins by contacting said keratins with a water-soluble cleansing composition, and removing said cleansing composition after cleansing is effected.

3. The method according to claim 2 wherein said modifying composition consists essentially of:
58.47 weight percent water;
19.49 weight percent milk protein product;
6.09 weight percent polysaccharide;
6.09 weight percent sodium hydroxide;
4.875 weight percent polyglycerol;
4.875 weight percent aqueous collagen polypeptide/amino acid solution; and
0.09 weight percent polysorbate-80.

4. The method according to claim 2 wherein said modifying composition consists essentially of:
58.65 weight percent water;
19.55 weight percent milk protein product;
6.11 weight percent polysaccharide;
5.80 weight percent sodium hydroxide;
4.89 weight percent polyglycerol;
4.89 weight percent aqueous collagen polypeptide/amino acid solution; and
0.09 weight percent polysorbate-80.

5. The method according to claim 2 wherein said modifying composition consists essentially of:
58.83 weight percent water;
19.61 weight percent milk protein product;
6.13 weight percent polysaccharide;
5.52 weight percent sodium hydroxide;
4.90 weight percent polyglycerol;
4.90 weight percent aqueous collagen polypeptide/amino acid solution; and
0.09 weight percent polysorbate-80.

6. The method according to claim 2 wherein said water-soluble cleansing composition is an acid-balanced cleansing composition having a pH from about 4.5 to 5.5.

7. A modifying composition for modifying filamentous keratins, having particular efficacy in straightening said keratins, consisting essentially of:
from about 58 to 60 weight percent water;
18 to 20 weight percent milk protein product;
6 to 6.25 weight percent polysaccharide;
5 to 6.5 weight percent sodium hydroxide;
4.75 to 5.25 weight percent polyglycerol;
4.75 to 5.25 weight percent aqueous collagen polypeptide/amino acid solution; and
0.075 to 0.095 weight percent polysorbate-80.

8. The modifying composition according to claim 7 consisting essentially of:
58.47 weight percent water;
19.49 weight percent milk protein product;
6.09 weight percent polysaccharide;
6.09 weight percent sodium hydroxide;
4.875 weight percent polyglycerol;
4.875 weight percent aqueous collagen polypeptide/amino acid solution; and
0.09 weight percent polysorbate-80.

9. The modifying composition according to claim 7 consisting essentially of:
58.65 weight percent water;
19.55 weight percent milk protein product;
6.11 weight percent polysaccharide;
5.80 weight percent sodium hydroxide;
4.89 weight percent polyglycerol
4.89 weight percent aqueous collagen polypeptide/amino acid solution; and
0.09 weight percent polysorbate-80.

10. The modifying composition according to claim 7 consisting essentially of:
58.83 weight percent water;
19.61 weight percent milk protein product;
6.13 weight percent polysaccharide;
5.52 weight percent sodium hydroxide;
4.90 weight percent polyglycerol;
4.90 weight percent aqueous collagen polypeptide/amino acid solution; and
0.09 weight percent polysorbate-80.

* * * * *

UNITED STATES PATENT AND TRADEMARK OFFICE
CERTIFICATE OF CORRECTION

PATENT NO. : 4,275,748
DATED : June 30, 1981
INVENTOR(S) : Helen V. Graziano

It is certified that error appears in the above-identified patent and that said Letters Patent are hereby corrected as shown below:

Column 1, line 28:

change "a oxidizing" to read

-- an oxidizing --

Column 3, line 20:

change "grow" to read

-- grows --

UNITED STATES PATENT AND TRADEMARK OFFICE
CERTIFICATE OF CORRECTION

PATENT NO. : 4,275,748          Page 2 of 5
DATED : June 30, 1981
INVENTOR(S) : Helen V. Graziano It is certified that error appears in the above—identified patent and that said Letters Patent are hereby corrected as shown below:

Column 6, line 37:

change "have previously" to read

-- have been previously -- line 40:

change "composition" to read

-- Composition -- line 64:

change "compositions" to read

-- Compositions --

UNITED STATES PATENT AND TRADEMARK OFFICE
CERTIFICATE OF CORRECTION

PATENT NO. : 4,275,748                    Page 3 of 5
DATED       : June 30, 1981
INVENTOR(S) : Helen V. Graziano It is certified that error appears in the above—identified patent and that said Letters Patent are hereby corrected as shown below:

line 65:

change "composition" to read

-- Composition -- line 67:

change "composition" to read

-- Composition --

Column 7, line 56:

change "log-standing" to read

-- long-standing --

UNITED STATES PATENT AND TRADEMARK OFFICE
CERTIFICATE OF CORRECTION

PATENT NO. : 4,275,748

DATED : June 30, 1981

INVENTOR(S) : Helen V. Graziano

It is certified that error appears in the above–identified patent and that said Letters Patent are hereby corrected as shown below:

Column 8, line 5:

change "reconsituted" to read

-- reconstituted -- line 16:

change "polygycerol" to read

-- polyglycerol --

Column 9, lines 31-32:

change "Laboratories)" to read

-- Laboratories); --

UNITED STATES PATENT AND TRADEMARK OFFICE
CERTIFICATE OF CORRECTION

PATENT NO. : 4,275,748  Page 5 of 5
DATED : June 30, 1981
INVENTOR(S) : Helen V. Graziano It is certified that error appears in the above-identified patent and that said Letters Patent are hereby corrected as shown below:

Column 11, line 9:

change "straignten" to read

-- straighten --

Column 14, line 25:

change "polyglycerol" to read

-- polyglycerol; --

Signed and Sealed this

Sixth Day of April 1982

[SEAL]

Attest:

GERALD J. MOSSINGHOFF

Attesting Officer    Commissioner of Patents and Trademarks